US011819506B2

(12) United States Patent
Havrileck et al.

(10) Patent No.: US 11,819,506 B2
(45) Date of Patent: Nov. 21, 2023

(54) USE OF GLUCOCORTICOIDS FOR THE TREATMENT OF EPITHELIAL MICROBIAL INFECTIONS OF A FLUID CONTAINING ORGAN WITH A NATURAL EXTERIOR ORIFICE IN MAMMALS

(71) Applicant: VIRBAC, Carros (FR)

(72) Inventors: Bertrand Havrileck, Nice (FR); Pierre Jasmin, Saint-Jeannet (FR); David McGahie, Ballymena (GB)

(73) Assignee: VIRBAC, Carros (FR)

( * ) Notice: Subject to any disclaimer, the term of this patent is extended or adjusted under 35 U.S.C. 154(b) by 0 days.

(21) Appl. No.: 17/263,516

(22) PCT Filed: Jul. 10, 2019

(86) PCT No.: PCT/EP2019/068619
§ 371 (c)(1),
(2) Date: Jan. 26, 2021

(87) PCT Pub. No.: WO2020/025283
PCT Pub. Date: Feb. 6, 2020

(65) Prior Publication Data
US 2022/0008439 A1 Jan. 13, 2022

(30) Foreign Application Priority Data

Jul. 30, 2018 (EP) .................................... 18306029

(51) Int. Cl.
*A61K 31/573* (2006.01)
*A61K 9/00* (2006.01)
*A61P 27/16* (2006.01)

(52) U.S. Cl.
CPC .......... *A61K 31/573* (2013.01); *A61K 9/0046* (2013.01); *A61P 27/16* (2018.01)

(58) Field of Classification Search
CPC .... A61K 31/573; A61K 9/0046; A61K 45/06; A61P 27/00; A61P 27/16
See application file for complete search history.

(56) References Cited

U.S. PATENT DOCUMENTS

| 2011/0263551 | A1 | 10/2011 | Slater |
| 2017/0042916 | A1* | 2/2017 | Hilliard .................. A61K 47/10 |
| 2017/0304409 | A1* | 10/2017 | Candioli Cravero ........................ A61K 31/7032 |

FOREIGN PATENT DOCUMENTS

| CN | 101 439 044 A | 5/2009 |
| CN | 105007922 A | 10/2015 |
| JP | 2010-511623 A | 4/2010 |
| WO | 2004054538 A1 | 7/2004 |
| WO | 2012/085068 A1 | 6/2012 |
| WO | 2014/131852 A1 | 9/2014 |

OTHER PUBLICATIONS

Rigaut et. al., Intern. J. Appl. Res. Vet. Med., publ. 2011, vol. 9(1), pp. 15-28 (Year: 2011).*
Oldenkamp et al., Veterinary Quarterly, publ. 1979, vol. 1(2), pp. 115-118 (Year: 1979).*
Bergvall et al., ECVD-ESVD abstracts, Veterinary Dermatology, vol. 28, p. 535, publ. 2017 (Year: 2017).*
Rème et al., Intern. J. Appl. Res. Vet. Med., vol. 8(1), pp. 1-6, publ. 2010 (Year: 2010).*
The International Bureau of WIPO, International Preliminary Report on Patentability issued in International Application No. PCT/EP2019/068619, dated Feb. 2, 2021, 8 pages.
Bensignor, E., et al., "Comparison of an Antifungal Agent With a Mixture of Antifungal, Antibiotic and Corticosteroid Agents for the Treatment of Malassezia Species Otitis in Dogs," Veterinary Record 158(6):193-195, Feb. 2006.
Emgard, P., et al., "Effects of Betamethasone Dipropionate Plus an Antihistamine in Patients With External Otitis," Current Therapeutic Research 60(7):364-370, Jul. 1999.
International Search Report dated Sep. 23, 2019, issued in International Patent Application No. PCT/EP2019/068619, filed Jul. 10, 2019, 5 pages.
Schmidt, V., et al., "Efficacy of a 0.0584% Hydrocortisone Aceponate Spray in Presumed Feline Allergic Dermatitis: An Open Label Pilot Study," Veterinary Dermatology 23(1):11-e4, Feb. 2012.
Kutz, Jr., J.W., et al., "Ciprofloxacin 0.3% + Dexamethasone 0.1% for the Treatment for Otitis Media," Expert Opinion on Pharmacotherapy 14(17):2399-2405, Oct. 2013.
Written Opinion dated Sep. 23, 2019, issued in International Patent Application Mo. PCT/EP2019/068619, filed Jul. 10, 2019, 7 pages.
Chinese First Office Action received for CN Application No. 201980050213.6, dated Apr. 13, 2023 with Translation of Office Action Text (38 pages total).
Japanese Office Action received for Japanese Application No. 2021-504392, received from Foreign Associate dated Apr. 4, 2023 in English (8 pages total).
Ordonez et al.; "Effective Treatment of Acute Diffuse Otitis Externa: I. A Controlled Comparison of Hydrocortisone-Acetic Acid, Nonaqueous and Hydrocortisone-Neomycin-Polymyxin B Otic Solutions"; Current Therapeutic Research; May Supplement 1978; pp. 883-8814 (13 pages total); vol. 23; No. 5; Therapeutic Research Press, Inc.
Rigaut et al.; "Efficacy of a Topical Ear Formulation With a Pump Delivery System for the Treatment of Infectious Otitis Externa in Dogs: a Randomized Controlled Trial"; Intern J. Appl. Res. Vet. Med.; 2011; pp. 15-28; vol. 9; No. 1.

(Continued)

*Primary Examiner* — Sarah Pihonak
(74) *Attorney, Agent, or Firm* — Christensen O'Connor Johnson Kindness PLLC

(57) ABSTRACT

The disclosure is directed to glucocorticoids for the treatment of epithelial microbial infections in fluid-containing organ having a natural exterior orifice in mammals; this new therapeutic use finds particular interest in the treatment of epithelial microbial infections of ear (such as otitis externa), udder (such as mastitis), and uterus (such as endometritis).

17 Claims, No Drawings

(56) References Cited

OTHER PUBLICATIONS

Sander, Robert; "Otitis Externa: A Practical Guide to Treatment and Prevention"; American Family Physician Mar. 1, 2001; pp. 927-936; vol. 63, No. 5.

Virbac AH, Inc.; "Easotic Otic—Hydrocortisone aceponate, miconazole nitrate, and gentamicin sulfate suspension" package insert of Easotic (R) Suspension; online Aug. 2011, searched Feb. 20, 2023; located at URL: https://fda.report/DailyMed/C2346AC2-270F-457B-BE1B-152DE1DCFDDA.pdf; 6 pages total.

European Examination Report dated Sep. 8, 2023, issued in corresponding European Application No. EP 19 740 521.0, 4 pages.

\* cited by examiner

USE OF GLUCOCORTICOIDS FOR THE TREATMENT OF EPITHELIAL MICROBIAL INFECTIONS OF A FLUID CONTAINING ORGAN WITH A NATURAL EXTERIOR ORIFICE IN MAMMALS

The present invention relates to non-invasive and antibiotic needless methods for treating epithelial microbial infections in mammals.

More specifically, the present invention is directed to glucocorticoids for the treatment of epithelial microbial infections in fluid-containing organ having a natural exterior orifice in mammals; this new therapeutic use finds particular interest in the treatment of epithelial microbial infections of ear (such as otitis externa), udder (such as mastitis), and uterus (such as endometritis).

Numerous animals and people are affected each year with otitis externa; i.e., a painful inflammation of the ear, often accompanied with a microbial infection of the affected tissue. Animals with ear flaps, such as many breeds of dogs, are especially susceptible. Their covered outer ear canals provide a sensitive environment for inflammation, favoring the local development of microbes to breed. A variety of bacteria, viruses, fungi and mites can be responsible for causing otitis externa.

Most otic disorders are the result of a painful inflammatory response to infections, allergic reactions or trauma to the ear. They are often of inflammatory origin with the bacteria taking advantage and overgrowing. The disordered local microbiome is the result of an incorrect inflammatory/anti-inflammatory balance. An otic infection can be associated with bacterial, fungal or viral infection and determination of the precise etiology is not practical since the organism is often difficult to isolate and cultivate.

External otitis in animal (contrary to human) is the first localization. Then on account of inflammation, tympanic membrane impairment reaches the middle ear (tympanic bullae). Tympanic membrane is able to heal and then both otitis can evoluate separately. Otitis externa (external ear infections), otitis media (middle ear infections) and otorrhea (otitis media with ruptured ear drum causing effusion) are among the most prevalent otic disorders.

Otitis externa, involving the ear canal portion of the external ear, is a common otological problem occurring mainly during hot, humid weather. In the incipient stage, symptoms include itching and pain in the ear canal, and tenderness when pressure is applied around the external auditory canal, the ear lobe is pulled or the jaw is moved. In some cases, suppuration can occur in the ear canal and hearing may be decreased. Over 90% of cases of otitis externa are due to inflammation associated with bacterial and fungal infections.

Otitis externa is usually treated with topical application of combined therapeutic agents demonstrating antimicrobial and/or antifungal activity as well as anti-inflammatory action. Broad spectrum topically effective antibiotic otic suspensions containing antibacterial agents, for example neomycin sulfate, colistin sulfate, polymyxin B, or combinations thereof, all broad spectrum in effect, are utilized to destroy causative bacteria. Antimycotic topically acting agents, for example nystatin and clotrimazole, are employed to destroy underlying fungal disease. In addition, the antiviral agent acyclovir is sometimes utilized to treat viral otitis externa including herpes zoster. Anti-inflammatory agents including, for example, hydrocortisone, hydrocortisone acetate and dexamethasone sodium phosphate, often included in the topically acting suspensions identified above, have been employed to control the inflammatory process of otitis externa. Most often, antimicrobial and anti-inflammatory agents are utilized in combination to treat the causative, triggering disorder, e.g., microbial infection, as well as the inflammatory process itself. They are also most often administered as suspensions in drop form for topical administration to the affected ear in order to enhance and provide a more uniform and sustainable delivery to the ear canal.

Example of a commercial product used to treat otitis externa in dog is Surolan®, which combines miconazole (antifungal), prednisolone (anti-inflammatory agent) and polymyxine B (antibiotic).

Another common epithelial microbial infection is mastitis, especially in domestic animals raised for obtaining milk such as a dairy cow and goat. Mastitis is a disease in which the mammary glands in the animals are infected with *Staphylococcus* (e.g., *Staphylococcus aureus*), *Streptococcus, Escherichia coli*, or another pathogenic bacterium causing inflammation; or a disease related to such a bacterium. Mastitis is a very costly disease for the dairy industry due to its high incidence, and the resulting reduced milk production, reduced milk quality and increased culling (removal) of animals from dairy herds. Mastitis is thus a very serious disease in domestic animals, and a known therapy frequently used is the administration by infusion of an antimicrobial drug directly into the mammary gland of a domestic animal affected with mastitis. Most of the mastitis is cured or alleviated by such an infusion for treating mastitis. However, due to a lowering of susceptibility of a bacterium causing mastitis to existing antimicrobial drugs for treating mastitis, at present mastitis for which no therapeutic effect is obtained by known drugs has increased.

Another organ with an exterior orifice in domesticated animals such as cattle commonly subject to epithelial microbial infections is the uterus. Metritis and endometritis are common infections of the uterus, where an incorrect inflammatory balance, usually post-calving, allows the development of microorganisms resulting in many metritis cases. The use of corticoids until now have been poorly effective.

Antimicrobial resistance has become a global burden for which inappropriate or excessive antimicrobial use is an important contributing factor. In this context, WHO developed several recommendations among them it encourages new non-antibiotic antimicrobials development.

In this context, the Inventors surprisingly found out that glucocorticoids, in particular hydrocortisone aceponate, that is well known for its anti-inflammatory activity, are able to treat epithelial microbial infections in fluid containing organ having a natural exterior orifice, such as but not limited to otitis externa in the ear, mastitis in the udder, and endometritis in the uterus, involving colonization of pathogenic microorganisms combined to an inflammatory state; this surprising effect is observed even without the administration of any antimicrobial agent. The administration of hydrocortisone aceponate (HCA) further leads to the restoration of a normal epithelial microbial flora. This observation is all the more surprising as corticosteroids are known to induce immunosuppressive effects.

The use of anti-inflammatory agent for the treatment of inflammation disorders of fluid-containing organs having an exterior orifice has been disclosed. The international application WO2004/082588 describes such use of anti-inflammatory agents (especially selective COX-2 inhibitory drugs), in specific formulations based with an amphipatic oil and a microcristallin wax, for the treatment of inflammatory disorders of the ear and udder. However, the use of anti-inflammatory agent, particularly of glucocorticoid agent for the treatment of microbial infections themselves has never been disclosed.

As discussed here above, inflammation of fluid containing organs having a natural exterior orifice may be associated with the development of microorganisms, conducting to an unbalanced microbial flora which develops abnormally.

Without being bound by theory, the inflammation itself may in fact be the cause of the abnormal microbial development. The epithelial inflammation promotes the bacteria development and a vicious circle maintains both inflammation and infection. Nowadays, inflammatory disorders as well as epithelial microbial infections such as otitis are treated with common treatments having an action on both inflammation and infection. Such treatments involve a combination of an antibiotic and/or an antifungal agent with an anti-inflammatory agent. They enable a punctual treatment of the infection, before frequent recurrences.

Nevertheless, the Inventors demonstrated that the use of glucocorticoids such as hydrocortisone aceponate (HCA) for treating the inflammation occurring in an epithelial microbial infection of a fluid containing organ having a natural exterior orifice resulted in the treatment of the infection itself.

Glucocorticoids, and in particular HCA, therefore present the advantage of enabling the treatment of both the inflammation and the infection, without affecting the natural microbial flora of the fluid-containing organ, on the contrary to the use of antibiotic and/or antifungal agents which do not only affect the microorganisms responsible of the infection but also affect the natural microflora. The unexpected effect of glucocorticoids on the treatment of infection advantageously decreases or avoids the use of other antimicrobial agent for the treatment of the infection. Glucocorticoids such as HCA allow a natural balance to reform, meaning the microbiome restabilises without the need to kill the pathogens, and allowing a more normal natural microbiome after treatment.

The Inventors also developed new formulations particularly adapted to an improved and efficient delivery of the glucocorticoid to the fluid containing organ having a natural exterior orifice. Those preferred formulations according to the invention present the advantage of having improved epithelial adhesive properties leading to a uniform and spread local coating of the area to be treated and therefore to provide a wider capacity of the anti-inflammatory agent to treat the infection locally.

The present invention thus relates to at least one glucocorticoid for use for the treatment and/or the prevention of epithelial microbial infections of a fluid containing organ having a natural exterior orifice in mammals, preferably a non-human mammal.

The terms "treat", "treating", "treatment" and "control", etc., as used herein, refer to any action providing a benefit to a subject afflicted with a condition or disease, including improvement in the condition through lessening or suppression of at least one symptom, delay in progression of the disease, prevention or delay in the onset of the disease, etc. The treatment of an epithelial microbial infection includes a reduction of the clinical symptoms of the epithelial microbial infection and/or an inhibition of the microbial overgrowth/multiplication of pathogenic bacteria, yeasts and/or fungi.

The areas aimed to be treated in the context of the present invention are fluid containing organs having an exterior orifice. Said organs comprise organs having a natural exterior orifice, such as the ears, the udders, the vagina, the uterus, the mouth, the nostrils . . . .

A fluid-containing organ having a natural exterior orifice according to the invention includes an ear of an animal. For example, in cats or dogs, the natural exterior orifice of the ear is the orifice of the external auditory canal.

A fluid-containing organ according to the invention also includes a mammary organ, for example an udder of a milk producing animal such as a cow, a goat or a sheep. A "milk producing animal" can be a female of any mammalian species but is preferably an animal raised for the purpose of providing milk, e. g., a cow, a goat or a sheep, and encompasses such animals whether or not they are lactating at the time of the inflammatory and/or infective condition or at the time of treatment. The natural exterior orifice of the mammary organ is the orifice of the teat canal.

A fluid containing organ further includes a vagina or uterus of an animal. The natural exterior orifice of the uterus is the vagina. The natural exterior orifice of the vagina is the vulva.

Other examples of fluid containing organ having a natural exterior orifice include the digestive tract and the respiratory tract.

Other protected cutaneous or external mucous areas of the body of animal may also be treated in the context of the present invention such as skin folds, genital area, underarm or underlegs of animals, interdigital area . . . .

Epithelial microbial infections according to the invention encompass infection-associated inflammatory disorders of the skin, epithelium or external mucous of a fluid containing organ comprising a natural exterior orifice due to pathogenic microorganisms including bacteria, yeasts and/or fungi. The term "infection" or "infected" may be defined herein by an (abnormal) microbial overgrowth/multiplication of pathogenic bacteria, yeasts and/or fungi.

Preferably, the present invention encompasses a glucocorticoid for use for the treatment and/or the prevention of an epithelial microbial infection of a fluid-containing organ having a natural exterior orifice selected from the group consisting of the ears, the udders and the uterus, in a mammal.

Preferably, the present invention encompasses a glucocorticoid for use for the treatment and/or the prevention of an epithelial microbial infection of a fluid-containing organ having a natural exterior orifice by topical application or topical administration of said glucocortocoid onto an epithelial area of the fluid-containing organ having a natural exterior orifice.

According to a preferred embodiment, the present invention relates to hydrocortisone or a salt thereof, preferably hydrocortisone aceponate, for use for the treatment and/or the prevention of an epithelial microbial infection of the ears in a non-human mammal; in such, said hydrocortisone or a salt thereof, preferably hydrocortisone aceptonate, is preferably used by topical administration onto an epithelial area of the ears.

Preferably, the present invention encompasses uses to treat subjects suffering from otitis externa infections including erythematous and ceruminous conditions (erythroceruminous otitis externa).

In a specific embodiment, otitis externa infection are non-suppurative or non purulent otitis and/or do not involve abnormal tympanic membrane, such as ruptured ear drum.

Preferably, epithelial microbial infections of the ear to be treated according to the invention may be caused by bacteria, fungi and/or yeasts; according to a preferred embodiment, said epithelial microbial infections of the ear to be treated is caused by bacteria, such as Gram-positive bacteria e.g. *Staphylococcus aureus* and *Streptococcus* spp. and Gram-negative bacteria *Escherichia coli*. According to another embodiment said epithelial microbial infections of the ear to be treated is caused by fungi and/or yeasts, e.g. *Trichophyton* spp., *Microsporum* spp., *Malassezia* spp. preferably *Malassezia pachydermatis*, *Candida* spp., in particular by *Malassezia* spp, preferably *Malassezia pachydermatis*.

In a most preferred embodiment, epithelial microbial infections of the ear to be treated according to the invention may be caused by Gram-positive bacteria e.g. *Staphylococcus aureus* and *Streptococcus* spp. and Gram-negative bacteria *Escherichia coli*, fungi and/or yeasts, e.g. *Malassezia pachydermatis*, *Candida* spp.

The use according to the present invention also allows the treatment of mastitis in a domestic animal (mammal).

In a preferred embodiment, the use according to the present invention also allows the treatment of mild mastitis in a domestic animal (mammal).

In a preferred embodiment, epithelial microbial infections of udder to be treated according to the invention may be caused by a bacteria selected from the group but not limited to *Staphylococcus* spp. (such as *S. aureus*, *S. chromogenes*, *S. epidermitis*, *S. hyicus*, *S. simulans*), *Escherichia coli*, *Klebsiella* spp., *Trueperella pyogenes*, *Streptococcus* spp. (such as *S. agalactiae*, *S. uberis*, *S. parauberis*, *S. salivarius*, *S. sanguinis*, *S. dysgalactiae*), *Corynebacterium* spp. (such as *C. bovis*), *Enterococcus* spp. (such as *E. faecium*, *E. faecalis*, *E. saccharolyticus*), *Pseudomonas* spp., *Mycoplasma* spp. (such as *M. bovis*, *M. alkalescens*, *M. bovigenitalium*, *M. bovirhinis*, *M. californicum*, *M. canadense*), *Prototheca* spp., *Candida* spp. (such as *C. kefyr*, *C. humicola*, *C. rugosa*, *C. inconspicua*, *C. krusei*, *C. lusitaniae*), *Rhodotorula*, *Trichosporon*, *Saccharomyces*, *Pichia*, *Cryptococcus*, *Aspergillus*, *Penicillum*, *Epicoccum*, *Phoma* and *Alternaria*.

In a most preferred embodiment, epithelial microbial infections of the udder to be treated according to the invention may be caused by *Streptococcus* spp., *Staphylococcus aureus*, *Escherichia coli*, *Klebsiella* spp., *Corynebacterium* spp., in particular *C. bovis*, *Mycoplasma* spp. and/or *Pseudomonas* spp.

In another embodiment, the use according to the present invention also allows the treatment of metritis and/or endometritis in a domestic animal (mammal).

In a preferred embodiment, epithelial microbial infections of the uterus to be treated according to the invention may be caused by a bacteria selected in the group but not limited to *Escherichia coli*, *Trueperella (Arcanobacterium) pyogenes*, Gram-negative anaerobic bacteria such as *Prevotella melaninogenica* and *Fusobacterium necrophorum*.

In another embodiment, the glucocorticoid is for use for the prevention of an epithelial microbial infection of a fluid containing organ having a natural exterior orifice in a mammal. The term "prevention" used according to the invention includes the prevention or reduction of risk of recurrence of an epithelial microbial infection of a fluid containing organ having a natural exterior orifice. The prevention of an epithelial microbial infection includes prevention or reduction of risk of recurrence of the clinical symptoms of the epithelial microbial infection and/or an inhibition of the microbial overgrowth/multiplication of pathogenic bacteria, yeasts and/or fungi.

More specifically, the present invention is useful for prevention of otitis externa, such as otitis including erythematous and ceruminous conditions, mastitis, endometritis and/or metritis.

The subject according to the invention is preferably a mammal, more preferably a non-human mammal, such as a domesticated farm animal (e.g., cow, horse, pig) or a pet (e.g., dog, cat).

In case the present invention aims to treat infectious otitis externa, the non-human mammal is preferably a companion animal, including but not limited to a dog or a cat.

Dogs frequently subjects of otitis externa include but are not limited to: dogs having covered outer ear canal and droopy ears (for example cocker, dachshund . . . ), abundant hairiness in the ear canal (for example, poodle, bichon . . . ), narrow ear canal (for example Shar-pei, French bulldog . . . ), hypersecretion of cerumen (for example, Belgian shepherd, German shepherd . . . ).

In a specific embodiment wherein the glucocorticoid according to the invention is for use in the prevention of otitis externa in a dog, the glucocorticoid is HCA and said dog is preferably not an atopic dog. Preferably said dog is a cocker.

In case the present invention aims to treat udder infections (mastitis), the mammal is preferably a non-human lactating mammal. Examples of non-human lactating mammals include ruminants, especially bovid such as cow, buffalo, but also goat, sheep, and camel. Preferably, the non human lactating mammal is a bovid, even more preferably said animal is a cow or a buffalo.

In case the present invention aims to treat uterus and/or vagina infections (metritis, endometritis), the mammal is preferably a mammal with a uterus. Examples of such mammals include but are not limited to humans, ruminants (bovid including e.g. cow, buffalo, but also goat, sheep, and camel) and sows. Preferably, said mammal is a non-human mammal, even more preferably said animal is a bovid including cows and buffalos.

In another embodiment, a subject according to the invention is a mammal with an epithelial microbial infection due to one or more pathogenic microorganisms which are resistant to conventional treatments like antibiotics.

Glucocorticoids (also called steroids, corticosteroids, or cortisone analogues) are compounds that are generally used for local application (nasal, cutaneous, ophthalmic, etc.); said glucocorticoid may be a monoester or a diester; preferably the glucocorticoid of the invention is a diester.

Glucocorticoid according to the invention may be selected in the group comprising alclometasone dipropionate, alclometasone propionate, amcinonide, beclomethasone dipropionate, betamethasone acetate, betamethasone dipropionate, betamethasone sodium phosphate, betamethasone benzoate, betamethasone valerate, budesonide, clobetasol propionate, clobetasol butyrate, clocortolone pivalate, desonide, dexamethasone acetate, dexamethasone nicotinate, dexamethasone propionate, dexamethasone valerate, dexamethasone sodium phosphate, desoximetasone, diflorasone diacetate, diflucortolone valerate, halobetasol propionate, flumethasone pivalate, fluocinolone acetonide, fluocinonide, flurandrenolide, fluticasone propionate, halcinonide, halobetasone propionate, halomethasone, a hydrocortisone such as benzodrocortisone (hydrocortisone 17-benzoate), hydrocortamate (hydrocortisone 21-(diethylamino)acetate), hydrocortisone aceponate (hydrocortisone 21-acetate 17α-propionate), hydrocortisone acetate, hydrocortisone bendazac, hydrocortisone buteprate (hydrocortisone 17α-butyrate 21-propionate), hydrocortisone butyrate (hydrocortisone 17α-butyrate), hydrocortisone 21-butyrate, hydrocortisone cypionate (hydrocortisone cyclopentanepropionate), hydrocortisone hydrogen succinate, hydrocortisone phosphate, hydrocortisone sodium phosphate, hydrocortisone sodium succinate, hydrocortisone succinate (hydrocortisone hemisuccinate), hydrocortisone tebutate, hydrocortisone valerate, hydrocortisone xanthogenic acid and hydrocortisone probutate; methylprednisolone acetate, methylprednisolone sodium succinate, methylprednisolone aceponate, mometasone furoate, prednisolone sodium phosphate, prednisolone acetate, prednisolone valerate, prednicarbate, prednisone, triamcinolone acetate, triamcinolone diacetate, triamcinolone acetonide, Preferably, the glucocorticoid is hydrocortisone or a salt thereof; more preferably glucocorticoid is hydrocortisone diester.

Even more preferably, the glucocorticoid according to the invention is hydrocortisone aceponate.

When used for the treatment and/or the prevention of epithelial microbial infections of a fluid containing organ having a natural exterior orifice in mammals, the at least one glucocorticoid is preferably formulated in a pharmaceutical composition that includes a pharmaceutically acceptable liquid or solid carrier or carriers.

According to a specific embodiment, the at least one glucocorticoid is the only active agent in the pharmaceutical composition; that is to say that said pharmaceutical composition does not contain any other active agent selected from antibiotic agent, antifungal agent or antiviral agent.

The present invention thus relates to a pharmaceutical composition comprising hydrocortisone or a salt thereof, preferably hydrocortisone aceponate, and a pharmaceutically acceptable carrier for the treatment and/or the prevention of an epithelial microbial infection of the ear in a non-human mammal, wherein said composition does not contain any antibiotic agent, antifungal agent and/or antiviral agent; preferably, said composition is administered by topical application onto an epithelial area of the ears.

According to the present invention, an active agent is a pharmaceutical or a veterinary compound showing a therapeutic effect, such compounds are also named Active Pharmaceutical Ingredient (API).

According to another specific embodiment, said pharmaceutical composition includes at least one further active ingredient in addition to said at least one glucocorticoids and said pharmaceutically acceptable liquid or solid carrier or carriers. The pharmaceutical composition then includes one or more active agents together with one or more of a variety of pharmaceutically acceptable carriers for delivery to a subject, including a variety of diluents or excipients known to those of ordinary skill in the art.

In a particular embodiment, said at least one further active ingredient is a non-antibiotic antimicrobial agent.

In animals especially, otitis externa is often linked to a parasitic infestation, most often an otocariosis, or Otodectes cynotis (ear mites) infestation. Topical treatment with ear mites has often been accomplished with relatively long courses of topical insecticidal therapy; e.g., with a pyrethrin-containing composition. However, shorter courses of therapy have been more recently obtained with mectin and mycin compounds; e.g., avermectins (such as ivermectin and selamectin) and milbemycin, administered otically, by injection, or on the skin. If clinically indicated, such antiparasiticidal compounds may be co-administered within, or as a separate adjunct to, the compositions of the invention. Further, where clinically indicated, anti-viral compounds, such as acyclovir, may be administered in lieu of, or as an adjunct to, antibiotic compounds.

Advantageously, pharmaceutical compositions according to the invention comprising a glucocorticoid and a further active ingredient as disclosed here above enables to reduce the quantity of the said further active ingredients due to the mode of action of the glucocorticoid itself. According to the demonstration of the inventors, the glucocorticoid is by itself capable of treating infection and therefore, its combined use to typical active ingredients used in the treatment of epithelial microbial infections of fluid containing organ having a natural exterior orifice results in an improved treatment of the infection; quantities of said other active ingredients can therefore be reduced.

The at least one glucocorticoid may also be administered together with a membrane restructuration protein such as glycoaminoglycan, ceramide, chitosan.

Another aspect of the invention is a composition comprising an active ingredient and a pharmaceutically acceptable carrier for the treatment of an epithelial microbial infection of a fluid-containing organ having a natural exterior orifice in a mammal, wherein said active ingredient is a glucocorticoid, preferably, hydrocortisone or a salt thereof, even more preferably hydrocortisone aceponate.

Another aspect of the invention is a pharmaceutical composition consisting of a glucocorticoid, preferably hydrocortisone or a salt thereof, even more preferably hydrocortisone aceponate, and a pharmaceutically acceptable carrier for the treatment and/or the prevention of an epithelial microbial infection of a fluid-containing organ having a natural exterior orifice, preferably the ear, in a mammal, preferably a non-human mammal.

A particularly preferred pharmaceutically acceptable carrier is methyl ether propylene glycol.

The composition for administration may additionally include additives, excipients, thickeners, and other substances which allow for more effective administration. Examples include oils, emollients, or other substances which increase the effectiveness and comfort of ear drops, nasal sprays, and inhalable compositions. This may also include substances which enhance the smell or taste.

Preferred compositions and formulations according to the invention provides a global coverage of the organ having a natural exterior orifice to be treated locally.

Preferred excipients are those showing an antiseptic activity, they may be selected in the group comprising, but not limited to alcohols (such as Alcohol Benzoate, benzyl alcohol, ethanol), solvents (for example Propylene glycol, Glycerine), surfactants, emollients (such as Macrogol Cetostearyl Ether, Diisopropyl Adipate), dispersing agents (such as nikkol so-15 VL Sorbitan sesqui olate), flavoring agents (for example vanillin), Chelating agents (for example EDTA disodium salt), oils (for example olive oil (including Oleic Acid, linolenic and linoleic acids), coconut oil, Caprilic/Capric Triglyceride, Coco-Caprylate/Caprate), extracts (essentials oil or not) (such as turmeic oil, *Melaleuca* oil, calendula, oregon grape, thyme, garlic, sage, lemon grass, thija, peppermint, catnip, tea tree, *hypericum*, rosemary, citrus, *eucalyptus*, avies *pectinata* wood oils), additives (for example Nitric oxide, sodium Benzoate, Silicon dioxide, Titanium dioxide, tanic acid, Curcumin (turmeric)), Polygodial, thymol, Nisine, polyhexanide, chlorbutanol, hydrogen peroxide, benzethonium chloride, silver (such as nitrate, chlorure or colloidal), silver salts, iodine or iodine derivated (such as Povidone (PVP) iodine), disinfecting agents (for example chlorhexidine, chloramine T, potassium permanganate), preservative agents (for example Bronopol, E-280

(propionic acid), E281 (sodium propionate), E282 (calcium propionate), E36 (formic acid), Phenoxyethanol, Thimerosal, potassium sorbate, Polylysine, citric acid, mix of citric (25%), sorbic (16.7%) acids, sodium Thiosulfate, sodium thiosulfate pentahydrate), sweetening agent (for example honey).

In a preferred embodiment, excipients having an antiseptic activity are selected in the group comprising Coco-Caprylate/Caprate, diisopropyl adipate, coconut oil, Nisine, PVP iodine, Alcohol Benzoate, Caprilic/Capric Triglyceride, Glycerine, olive oil (including Oleic Acid, linolenic and linoleic acids), Polylysine, Honey, Propylene glycol, Macrogol Cetostearyl Ether, nikkol so-15 VL Sorbitan sesquiolate, Silica dioxide.

In a more preferred embodiment, excipients having an antiseptic activity are PVP iodine, Coco-Caprylate/Caprate, diisopropyl adipate, coconut oil and Nisine.

A particularly preferred pharmaceutically acceptable carrier is methyl ether propylene glycol.

Other examples of formulations for topical application of glucocorticoid such as HCA particularly adapted for an otic administration include:

Suspension of lipid based particles with a solid matrix, preferably Solid Lipid Nanoparticles (SLN) and Nanostructures Lipid Carriers (NLC), comprising at least one lipid and preferably at least one emulsifier. The lipid particles being solid at room temperature, they can therefore comprise a single solid lipid or a mixture of lipids that may partly contain at least one solid lipid.

Suitable solid lipids are for example:
Hydrocarbons, such as solid paraffins;
Fatty acids, such as myristic acid, palmitic acid, stearic acid;
Monoglycerides, such as glyceryl monostearate, glyceryl hydroxystearate, glyceryl benehate;
Diglycerides, such as glyceryl palmitostearate;
Triglycerides, such as glyceryl tristearate, glyceryl trimyristate, hydrogenated castor oil, hydrogenated palm oil;
Waxes, such as beeswax, carnauba wax, cetyl palmitate.

A preferred solid lipid is glyceryl palmitostearate.

Suitable non solid lipids are for example:
Hydrocarbons, such as liquid paraffin, squalene (unsaturated hydrocarbon);
Vegetable oils, such as soy bean oil, castor oil;
Fatty esters, such as isopropyl myristate;
Medium chain triglycerides, such as caprylic-capric triglycerides;
Fatty acids, such as oleic acid, linoleic acid;
Propylene glycol fatty acid ester, such as propylene glycol dicaprylocaprate;
Vitamin E.

The melting temperature range of solid lipids is preferably 30° C.-100° C. and more preferably 40° C.-90° C. When used in combination with non-solid lipids, solid lipids can have a melting temperature that is lower or higher than the 30° C.-100° C. range.

Generally, at least one surfactant is needed to aid in the dispersion process of the melted lipid(s) in the heated aqueous phase required to form a suspension of lipid based particles with a solid matrix and to stabilize the lipid particles dispersion after cooling.

Many class of surfactants, lipophilic or hydrophilic, can be used in the preparation and stabilization of lipid particles suspension:

Non-ionic surfactants, such as polyoxyethylene sorbitan fatty acid esters, sorbitan esters, macrogol 15 hydroxystearate, glyceryl monostearate, polyoxyethylene castor oil derivatives, polyoxylglycerides, glyceryl stearate and PEG-75 stearate, cetyl alcohol and ceteth-20 and steareth-20;

Anionic surfactants, such as sodium dodecyl sulphate, sodium deoxycholate, sodium glycocholate, sodium oleate;

Cationic surfactants, such as benzalkonium chloride, cetrimide, stearylamine;

Amphoteric surfactants, such as egg lecithin, soya lecithin, phosphatidylcholines, egg phospholipids, soya phospholipids, phosphatidylethanolamines;

Block copolymers, such as poloxamers.

A combination of surfactants can be used, the choice of the surfactant(s) depending on the lipid(s) used.

Preferably, non-ionic surfactants are used and more preferably the surfactants are chosen from the polyoxyethylene sorbitan fatty acid esters group. A preferred surfactant is polysorbate 80.

Other excipients such as thickeners, emollients, co-surfactants, buffering agents, pH regulating agents, salts, antioxidants and preservatives can be used for composition stability, more effective administration and comfort of compositions.

A suspension of lipid based particles with a solid matrix can be prepared according to various standard methods. The preferred method is high-shear homogenization followed by ultrasonication. The lipid phase that can contain at least surfactant(s) is melted. The glucocorticoid is preferably dissolved or dispersed in the molten lipid. An aqueous phase of the same temperature as the molten lipid phase and that can contain at least surfactant(s) is added to the lipid phase. The API may nevertheless be in an aqueous phase. The mixture is then passed through a high-shear mixer to create a coarse emulsion, followed by ultrasonication. The choice of the process parameters depends on the equipment and on the compositions.

In situ gelling systems that are liquid or viscous at room temperature and that undergo gelation at body temperature, comprising at least one polymer showing thermoreversible gelation property, such as poloxamers.

A preferred polymer showing thermoreversible gelation property is poloxamer 407.

Other excipients such as thickeners, solvents, emollients, co-surfactants, buffering agents, pH regulating agents, salts, antioxidants and preservatives can be used for composition stability, more effective administration and comfort of compositions.

An in situ gelling systems suspension can be prepared according to various methods. Preferably, all ingredients, except the poloxamer(s), are dissolved or dispersed in water. The poloxamer(s) is then dissolved in the approximately 5° C. pre-cooled aqueous mixing. The active ingredient can be added alone or in combination with other excipient(s) in the aqueous phase containing the polymer such as poloxamer(s) at 5° C.

In situ phospholidpid gelling systems: said systems are fluid and undergo gelation once they are in contact with water. This is particularly adapted to otic administration after a clean up of the ear before the treatment administration. Said gelling systems enable a better residency of the product locally. Such systems may comprises at least one phospholipid, such as phosphatidylcholine derivatives.

A preferred jellifying agent is Phospholipon 90G.

Other excipients such as thickeners, solvents, emollients, co-surfactants, buffering agents, pH regulating agents, salts, antioxidants and preservatives can be used for composition stability, more effective administration and comfort of compositions.

Examples of preferred solvents include isopropyl myristate and ethanol.

Jellified formulations, which present improved viscosity and therefore enables an improved residency of the product in the ear. Such formulations may cromprise thickeners. Examples of thickeners comprises Povidone K90, Glycerol, PEG400, Carbomers (Acrypol® 971)/acrylic polymers, Hypromellose (Hydroxypropyl Methylcellulose 2910 60HD6), Hydroxypropyl methyl cellulose and other common thickeners (gums, poloxamers). Preferred thickeners are Povidone K90 and glycerol.

Other excipients such as solvents, emollients, co-surfactants, buffering agents, pH regulating agents, salts, antioxidants and preservatives can be used for composition stability, more effective administration and comfort of compositions.

Micellar solutions, comprising at least one dispersed surfactant. At least one non solid lipid can be added.

Suitable surfactants are preferably hydrophilic, exhibiting a high hydrophilic-lipophilic balance value, being soluble in water and acting as solubilizing agents for lipophilic substances by keeping these in micellar solution. More preferably, surfactants are non-ionic such as polyoxyethylene sorbitan fatty acid esters, polyoxyethylene castor oil derivatives, macrogol 15 hydroxystearate, polyoxylglycerides and poloxamers.

A preferred surfactant is polysorbate 80.

Other excipients such as thickeners, solvents, emollients, co-surfactants, buffering agents, pH regulating agents, salts, antioxidants and preservatives can be used for composition stability, more effective administration and comfort of compositions.

Micellar solutions are prepared by adding sufficient surfactant concentration in a liquid medium to form the micellar solution Surfactant(s) concentration should be above the critical micellar concentration to predominantly form micelles. The lipophilic substance(s) is then added and solubilized by the micellar solution under gentle agitation.

Cyclodextrin inclusion complexes, comprising at least one cyclodextrin acting as solubilizing agents for lipophilic substances by keeping these entrapped in the hydrophobic internal cavity of the solubilized cyclodextrin molecules.

Other excipients such as thickeners, solvents, emollients, co-surfactants, buffering agents, pH regulating agents, salts, antioxidants and preservatives can be used for composition stability, more effective administration and comfort of compositions.

A preferred cyclodextrin is hydroxypropyl-beta-cyclodextrin.

Aqueous cyclodextrin inclusion complexes are prepared by adding cyclodextrin(s) in aqueous medium. The lipophilic substance(s) is then added and solubilized by the cyclodextrin(s) molecules under gentle agitation.

Other excipients such as thickeners, solvents, emollients, co-surfactants, buffering agents, pH regulating agents, salts, antioxidants and preservatives can be used for composition stability, more effective administration and comfort of compositions.

Oil/Water or water/oil Emulsions: emulsions comprising at least one lipid, at least one emulsifier and at least water.

Suitable lipids are for example:
Hydrocarbons, such as solid paraffins, liquid paraffin, squalene (unsaturated hydrocarbon);
Fatty acids, such as myristic acid, palmitic acid, stearic acid;
Monoglycerides, such as glyceryl monostearate, glyceryl hydroxystearate, glyceryl benehate;
Diglycerides, such as glyceryl palmitostearate;
Triglycerides, such as glyceryl tristearate, glyceryl trimyristate, hydrogenated castor oil, hydrogenated palm oil, soy bean oil, castor oil, caprylic-capric triglycerides;
Waxes, such as beeswax, carnauba wax, cetyl palmitate;
Fatty esters, such as isopropyl myristate;
Fatty acids, such as oleic acid, linoleic acid;
Propylene glycol fatty acid ester, such as propylene glycol dicaprylocaprate;
Vitamin E.

Generally, at least one surfactant is needed to aid in the dispersion process and to stabilize the emulsion. A combination of surfactants can be used.

Many class of surfactants, lipophilic or hydrophilic, can be used:
Non-ionic surfactants, such as polyoxyethylene sorbitan fatty acid esters, sorbitan esters, macrogol 15 hydroxystearate, glyceryl monostearate, polyoxyethylene castor oil derivatives, polyoxylglycerides, glyceryl stearate and PEG-75 stearate, cetyl alcohol and ceteth-20 and steareth-20;
Anionic surfactants, such as sodium dodecyl sulphate, sodium deoxycholate, sodium glycocholate, sodium oleate;
Cationic surfactants, such as benzalkonium chloride, cetrimide, stearylamine;
Amphoteric surfactants, such as egg lecithin, soya lecithin, phosphatidylcholines, egg phospholipids, soya phospholipids, phosphatidylethanolamines;
Block copolymers, such as poloxamers.

Preferably, non-ionic surfactants are used.

Other excipients such as thickeners, emollients, co-surfactants, buffering agents, pH regulating agents, salts, antioxidants and preservatives can be used for composition stability, more effective administration and comfort of compositions.

Formulations particularly adapted to treat mastitis for non-human animals, also called intramammary infusion, are usually composed of a vehicle or carrier associated with an active ingredient. Intramammary formula can be in the form of a liquid product, a semi-solid or a thixotropic product such as a solution, a suspension, a paste, a gel, or a cream formulation.

In a preferred embodiment the composition according to the invention comprises at least one glucocorticoid, as described above, which is solubilized in the pharmaceutically acceptable carrier. In another preferred embodiment, the glucocorticoid according to the invention is in the form of particles in the intramammary formulations.

The intramammary composition of the invention may further comprise any suitable pharmaceutically acceptable ingredients which are known in the pharmaceutical art, selected from the groups consisting of: oil, medium chain triglyceride, wax (e.g. microcrystalline), fatty acid, fatty acid derivatives, viscosity control agent or thickener (stearate salt, silicon dioxide, cellulose); pigment, opacifier, dispersing agent; emulsifier; stabilizer; surfactant, humectant; antioxidant; antibacterial agent, antifungal agent, preservative, emollient, polymers, any compound conferring organoleptic properties (flavor, dye, perfume, etc.), water, and combinations thereof. The oil used is selected from vegetable (e.g. natural plant oil) or mineral origin (e.g. paraffin, white petrolatum, yellow petrolatum, etc.). The fatty acid derivatives are either organic or inorganic compounds such as aluminium stearate, magnesium stearate, zinc stearate, stearic acid, hydrogenated vegetable oil and the like. Mineral particles such as, but not only, silica, clay, calcium carbonate are eventual excipients that can be used as thickener. The formula can also comprise a non-toxic heavy metal.

An intramammary infusion comprising a glucocorticoid according to the invention in the form of particles which may be encapsulated in the pharmaceutically acceptable carrier targets a protection with a long lasting effect, to ensure the desired treatment time and efficacy.

Compositions according to the invention can be administered through various administration routes, including but not limited to topical, or oral administrations, especially when the target is digestive tract and intestinal epithelium.

Preferably, compositions according to the invention are administered by topical application or topical administration onto an epithelial area of the fluid-containing organ having a natural exterior orifice. Particularly, said compositions are administered by topical application or topical administration into, i.e. inside the cavity of, the fluid containing organ having a natural exterior orifice, i.e. through the orifice of said fluid-containing organ and onto an epithelial area of said fluid-containing organ affected by the microbial disorder.

Preferably, the present invention also provides methods for topically treating epithelial microbial infections through topical administration of glucocorticoids on said epithelia of a fluid containing organs having a natural exterior orifice, particularly into, i.e. inside the cavity of, the fluid containing organ having a natural exterior orifice, i.e. through the orifice of said fluid-containing organ and onto an epithelial area of said fluid-containing organ affected by the microbial disorder.

By "topical administration" is meant that the at least one glucocorticoid used according to the invention is applied onto the epithelial area that is (treatment) or that has been (prevention of recurrence) affected by the microbial disorder.

In a particular embodiment, the at least one glucocorticoid, preferably hydrocortisone or a salt thereof, even more preferably hydrocortisone aceponate, used according to the invention is applied to the external ear canal; i.e., on the outer ear side of the tympanic membrane (eardrum). Topical administration to the outer ear canal is achieved via, for example, introducing the composition of the invention into the outer ear canal via any medically acceptable means; e.g., by applying the carrier composition to the membrane by insertion of a needleless syringe, dropper or swab into the auditory canal. Administration is repeated as required to achieve the therapeutically effective dosage level for the glucocorticoid compound given.

Where the method of the invention comprises injection or infusion of the at least one glucocorticoid into an udder via the teat canal or into the uterus via the vagina, it can provide effective treatment of mastitis and metritis/endometritis, respectively. "Intramammary infusion" is an operation wherein a liquid composition is caused to flow into an udder (into the teat cistern and/or the gland cistern) via a teat canal, regardless of the timescale involved. "Uterus infusion" is an operation wherein a liquid composition is caused to flow into the uterus via the vagina, regardless of the timescale involved. In the present context, "infusion" and "injection" are substantially synonymous.

In a particular embodiment, the at least one glucocorticoid can be administered for treatment of mastitis by inserting the cannula nozzle of a mastitis syringe into the external orifice of the teat canal of an udder of a milk producing animal and infusing the at least one glucocorticoid into the udder.

In a particular embodiment, the at least one glucocorticoid can be administered for treatment of metritis and/or endometritis by inserting the cannula nozzle of a syringe into the vagina of the mammal having a uterus and infusing the at least one glucocorticoid into the vagina and/or the uterus of said animal.

For the treatment and the prevention of epithelial microbial infections of a fluid containing organs having a natural exterior orifice encompassed by the present invention, a quantity of 0.01 to 150 mg of glucocorticoid is administered at each administration. Accordingly, the pharmaceutical composition of the invention comprises a content of glucocorticoid chosen so that a single dose of said pharmaceutical composition comprises the required quantity of glucocorticoid.

Such glucocorticoid may be administered once or twice a day for 1 to 20 days; depending on the infection importance, the glucocorticoid may be administered for 1, 2, 3, 4, 5, 6, 7, 8, 9, 10, 11, 12, 13, 14, 15, 16, 17, 18, 19 or 20 days (i.e. up to 20 days).

In the specific case of the treatment of otitis externa, the quantity of glucocorticoid, preferably hydrocortisone or a salt thereof, even more preferably hydrocortisone aceponate, to be applied is preferably comprised between 0.01 and 10 mg; such glucocorticoid may be administered once or twice a day for 2 to 20 days; depending on the infection importance, the glucocorticoid may be administered for 2, 3, 4, 5, 6, 7, 8, 9, 10, 11, 12, 13, 14, 15, 16, 17, 18, 19 or 20 days.

Preferably, for the treatment of otitis externa the quantity of glucocortoid, preferably hydrocortisone or a salt thereof, even more preferably hydrocortisone aceponate, to be administered is comprised between 0.05 and 5 mg, even more preferably between 0.1 and 1.2 mg. Even more preferably, the quantity of glucocorticoid is comprised between 0.1 to 0.5 mg. In a most preferred embodiment, said quantity is comprised between 0.25 to 0.3 mg.

For example, 0.5 ml of a pharmaceutical composition according to the invention is used and in which the content of glucocorticoid in said pharmaceutical composition is 0,584 mg/ml.

In another preferred embodiment, said glucocorticoid, preferably hydrocortisone or a salt thereof, even more preferably hydrocortisone aceponate, for use in the treatment of otitis externa is applied once or twice daily from 1 to 14 days, and preferably from 7 to 14 days, in the ear. In a most preferred embodiment, said glucocorticoid for use in the treatment of externa otitis is administered once daily for 7 to 14 days.

According to a preferred embodiment related to the treatment of externa otitis, the quantity of glucocorticoid, preferably hydrocortisone or a salt thereof, even more preferably hydrocortisone aceponate, to be administered is comprised between 0.1 to 0.5 mg and is administered once daily for 7 to 14 days, preferably for 7 days.

According to a more preferred embodiment related to the treatment of externa otitis, said pharmaceutical composition comprises HCA. Preferably the animal is a dog. Preferably said dog is not an atopic dog. Preferably, said dog is a cocker.

According to another embodiment, the treatment may be administered sequentially. The term "sequentially" or "sequential treatment" corresponds to an administration of the glucocorticoid over a first period of treatment, followed by a second period where the treatment is stopped, followed by an additional period of treatment. The sequential treatment may be repeated as long as necessary.

According to another embodiment related to the prevention of externa otitis, the quantity of glucocorticoid, preferably hydrocortisone or a salt thereof, even more preferably hydrocortisone aceponate, to be administered is comprised between 0.01 and 10 mg and is administered at least once a week in the ear for 10 to 20 weeks.

Preferably, for the prevention of otitis externa, the quantity of glucocortoid, preferably hydrocortisone or a salt thereof, even more preferably hydrocortisone aceponate, to be administered is comprised between 0.05 and 5 mg, even more preferably between 0.1 and 1.2 mg. Even more preferably, the quantity of glucocorticoid is comprised between 0.1 to 0.5 mg. In a most preferred embodiment, said quantity is 0.25 to 0.3 mg.

Preferably said glucocorticoid is HCA. Preferably the animal is a dog. Preferably said dog is not an atopic dog. Preferably, said dog is a cocker.

In another preferred embodiment, said pharmaceutical composition comprising a glucocorticoid, preferably hydrocortisone or a salt thereof, even more preferably hydrocortisone aceponate, for use in the prevention of otitis externa is applied in the ear at least once a week, preferably twice a week for 10 to 20 weeks, preferably 12 to 18 weeks, even more preferably for 16 weeks. Preferably, the composition is administered on two consecutive days per week.

According to a preferred embodiment related to the treatment of externa otitis, of the quantity of glucocorticoid, preferably hydrocortisone or a salt thereof, even more preferably hydrocortisone aceponate, to be administered is comprised between 0.1 to 0.5 mg and is administered in the ear twice a week for 16 weeks.

Preferably said glucocorticoid is HCA. Preferably the animal is a dog. Preferably said dog is not an atopic dog. Preferably, said dog is a cocker.

In the specific case of the treatment of mastitis, the quantity of glucocorticoid to be applied in the udder via the teat canal is preferably comprised between 1 and 50 mg; such glucocorticoid may be administered at least once a day for 1 to 10 days; depending on the infection importance, the glucocorticoid may be administered for 1, 2, 3, 4, 5, 6, 7, 8, 9 or 10 days.

Preferably, the quantity of glucocorticoid to be administered is comprised between 10 and 40 mg, even more preferably between 15 and 25 mg. A most preferred embodiment is a dose of glucocorticoid of 20 mg.

For example, a volume of 10 ml of a pharmaceutical composition comprising the glucocorticoid according to the invention is administered in the udder via the teat canal and the concentration of said glucocorticoid in said pharmaceutical composition is preferably comprised between 0.05 and 1% w/w, preferably 0.2%.

Preferably, the pharmaceutical composition for the treatment of mastitis comprising a glucocorticoid according to the invention is administered in the udder via the teat canal once or twice per day, preferably twice per day, for 1 to 10 days, preferably for 1 to 5 days, and even more preferably for 1 up to 2 days.

In a most preferred embodiment, the glucocorticoid according to the invention is administered in the udder via the teat canal with a quantity of glucocorticoid comprised between 10 and 40 mg twice per day for up to 2 days.

In a preferred embodiment, each teat of the udder of the mammal is treated with a pharmaceutical composition according to the invention. Preferably said glucocorticoid is HCA. Preferably the animal is a cow.

According to another embodiment related to the prevention of mastitis, the quantity of glucocorticoid to be administered is comprised between 0.01 and 50 mg, preferably between 10 and 40 mg, even more preferably between 15 and 25 mg and is administered in the udder via the teat canal at least once a week. Preferably said glucocorticoid is HCA. Preferably the animal is a cow.

In the specific case of the treatment of metritis/endometritis, the quantity of glucocorticoid to be applied in the uterus is preferably comprised between 1 and 150 mg, preferably between 10 and 120 mg, even more preferably between 30 and 120 mg.

According to one embodiment related to the treatment of metritis/endometritis, said glucocorticoid may be administered once or several times. In a preferred embodiment, said glucocorticoid is administered once. Preferably said glucocorticoid is HCA.

According to another embodiment related to the prevention of metritis/endometritis, the quantity of glucocorticoid is comprised between 1 and 150 mg, preferably between 10 and 120 mg, even more preferably between 30 and 120 mg, and is administered in the uterus once or several times.

The present invention further provides a method of prevention or treatment of an epithelial microbial infection of a fluid containing organs having a natural exterior orifice, preferably the ear, the method comprising administering topically at least one glucocorticoid, preferably hydrocortisone or a salt thereof, even more preferably hydrocortisone aceponate, to said epithelium affected by said microbial infection.

Another aspect of the invention is a kit comprising:
a) a pharmaceutical composition according to the invention,
b) a notice of use of the product, and
c) an optional administration device.

Said pharmaceutical composition in the kit according to the invention may be provided in a ready-to-use administration device or may be provided separately from the administration device.

Examples of administration device include, but are not limited to, pump spray, syringe, tube.

A particularly adapted administration device for the treatment and/or prevention of otitis externa is a pump with a canula.

A particularly adapted administration device for the treatment and/or prevention of mastitis, metritis and/or endometritis is a syringe.

EXAMPLE 1—EVALUATION OF THE EFFICACY OF HYDROCORTISONE ACEPONATE (HCA) FORMULATION (CORTAVANCE®) FOR THE TREATMENT OF OTITIS EXTERNA IN DOGS

Objectives: Erythroceruminous otitis is mainly due to inflammation while microbial proliferation being only a secondary manifestation of the disease. The efficacy of local corticotherapy with Hydrocortisone aceponate (HCA) as a stand-alone therapy has been previously evaluated for the prevention of relapse of allergic otitis, but there is no convincing data in veterinary medicine about its use for the treatment of an acute flare of otitis externa. The main objective of this study was to evaluate if the use of HCA alone in the ear canal can be effective in the treatment of otitis externa in dogs.

Cortavance® product is composed of 0.0584% of Hydrocortisone aceponate in Propylene glycol methyl ether (QSP 100%).

Materials and methods: Dogs with clinical (OTIS3 score ≥4) and cytological (score >1) signs of acute episode of otitis externa (erythroceruminous, non-parasitic), were included in this double-blinded, randomized, controlled, multicenter clinical field trial. Dogs were allocated in two groups and the ear canal was treated with 0.5 mL of HCA (Cortavance® group) once daily or 0.5 mL of a pharmaceutical veterinary treatment Surolan® comprising a combination of an anti-fungal, anti-inflammatory and antibiotic agents (miconazole, prednisolone and polymyxine B) (Surolan® group) twice daily, for 7 days or 14 days if symptoms persisted. At D7, D14 and D28, clinical OTIS3 score (according to Nuttal and Bensignor, Vet dermatol, 2014), cytological score (according to Budach and Mueller, Vet Derm, 2012) and pruritus (according to Rybnicek and al, Vet Derm, 2008) were compared to baseline. The treatment was considered as a success if remission occurred on D7 or D14 with no relapse at D28.

Results: Fifty three dogs with unilateral or bilateral otitis externa were enrolled in this clinical field trial, but 4 dogs were excluded from the analysis because of non-compliance to the protocol (dogs only seen the first or the first two follow-up visits). The analysis was performed on 49 dogs (73 ears): 23 dogs (34 ears) and 26 dogs (39 ears) were allocated in Cortavance® group and Surolan® group respectively.

At baseline, homogeneity was respected between Cortavance® vs Surolan® groups respectively for body weight (21.42 kg±13.61 vs 19.05 kg±16.11, Wilcoxon's test $p=0.37$), otitis unilateral or bilateral (52.2% vs 50.0% unilateral or 47.8% vs 50.0% bilateral, Chi-square test $p=0.88$), clinical score OTIS3 (6.2±0.9 vs 6.0±1.4, Wilcoxon's test $p=0.35$), global cytological score (4.0±1.6 vs 4.5±1.7, Wilcoxon's test $p=0.24$), type of otitis (bacteria: 5.9% vs 5.1%, bacteria and *Malassezia*: 61.8% vs 74.4%, *Malassezia*: 32.3% vs 20.5%, Fisher's exact test $p=0.47$) and pruritus score (5.9±1.8 vs 5.7±2.2, Student's test $p=0.72$). The dogs were significantly younger (4.24 years±3.26 vs 6.16 years±3.30, Wilcoxon's test $p=0.02$) for the group Cortavance® vs group Surolan® respectively.

At D7, both treatment improved clinical, cytological and pruritus signs with a success rate not significantly higher (50.0% vs 30.8%, Chi-square's test $p=0.09$) for Cortavance® vs Surolan® respectively. While global cytological score reduction were similar between groups (61.5%±23.4 vs 61.7%±22.7, Wilcoxon's test $p=0.89$), clinical score reduction (62.7%±22.6 vs 46.3%±20.8, Student's test $p=0.002$) and pruritus reduction (70.0%±17.5 vs 57.1%±25.3, Student's test $p=0.047$) were significantly higher for Cortavance® vs Surolan® respectively.

At D14, the success rate was similar (74.1% vs 73.5%, Chi-square's test $p=0.96$) and clinical score reduction (82.3%±15.4 vs 77.6%±18.5, Wilcoxon's test $p=0.27$), global cytological score reduction (82.2%±26.7 vs 76.2%±28.3, Wilcoxon's test $p=0.31$) and pruritus reduction (88.9%±9.8 vs 80.5%±19.2, Wilcoxon's test $p=0.15$) were not significantly higher for Cortavance® vs Surolan® respectively.

At D28, the no relapse rate was not significantly lower (83.3% vs 95.2%, Fisher's exact test $p=0.35$) and clinical score reduction (80.2%±24.3 vs 71.1%±22.7, Wilcoxon's test $p=0.07$), cytological score reduction (84.1%±19.7 vs 73.5%±26.1, Wilcoxon's test $p=0.09$) and pruritus reduction (86.1%±20.0 vs 76.3%±21.4, Wilcoxon's test $p=0.08$) were not significantly higher for Cortavance® vs Surolan® respectively.

A complementary analysis was performed by considering individually the cytological scores for Bacteria, *Malassezia* and Neutrophils. Score for Bacteria compared to baseline was reduced by 58.7%±35.1 vs 49.7%±34.5 (Wilcoxon's test $p=0.45$) at D7, 84.4%±30.1 vs 69.9%±39.2 (Wilcoxon's test $p=0.22$) at D14 and 80.3%±22.8 vs 70.8%±34.4 (Wilcoxon's test $p=0.44$) at D28 for Cortavance® vs Surolan® respectively. Score for *Malassezia* compared to baseline was reduced by 58.6%±31.9 vs 63.1%±26.8 (Wilcoxon's test $p=0.64$) at D7, 79.2%±31.4 vs 77.8%±41.3 (Wilcoxon's test $p=0.87$) at D14 and 84.1%±23.6 vs 72.8%±37.5 (Wilcoxon's test $p=0.28$) at D28 for Cortavance® vs Surolan® respectively. Note that only one ear had an increase in *Malassezia* score during the course of the study and that this ear was in Surolan® group. Score for Neutrophils compared to baseline was reduced by 75.0%±46.3 vs 58.3%±46.9 (Wilcoxon's test $p=0.41$) at D7, 100%±0.0 vs 81.8%±40.5 (Wilcoxon's test $p=0.28$) at D14 and 100% vs 100% at D28 for Cortavance® vs Surolan® respectively.

The global success rate was not significantly higher (60.6% vs 57.1%, Chi-square's test $p=0.77$) for Cortavance® compared to Surolan® respectively. Moreover statistical analysis further emphasis the better onset of action of Cortavance® from D7, where both pruritus and clinical score are significantly lower compared to Surolan®.

No adverse events were recorded during the trial.

Conclusion: This clinical field study highlights that HCA is at least as effective as a reference treatment comprising anti-inflammatory, antibiotic and antifungal agents in treating erythemato ceruminous otitis externa in dogs, and to control bacterial and fungal proliferations.

EXAMPLE 2—EVALUATION OF THE EFFICACY OF HYDROCORTISONE ACEPONATE (HCA) FORMULATION FOR THE INTRAMAMMARY TREATMENT OF MASTITIS IN LACTATING COWS AND HEIFERS

The purpose of this multicenter clinical field study is to evaluate the efficacy and the safety of HCA at a dosage of 20 mg in 10 ml of Vaseline oil based formulation every 12±2 h hours (minimum of one and maximum of four treatments) in the intramammary treatment of mild clinical mastitis in lactating cows; more specifically to assess the efficacy (clinical cure rate) of HCA alone in the treatment of udder inflammation (mild clinical mastitis), under field conditions and to assess the safety and the risk of aggravation or relapses during and after the treatment with HCA alone.

Animals (50 lactating cows and heifers presenting clinical symptoms of mastitis) have been intramammarily treated with one syringe (10 mL) containing 20 mg of HCA at each time point for a minimum of 1 and a maximum of 4 treatments in a 12±2 h interval (each morning or evening milking time, respectively). Depending on the result of the clinical examination and the clinical status classification, the animal have been treated until the animal was classified as clinically cured, failure or the maximum of 4 treatments is reached.

Before the tested treatment, a sample of milk of each animal has been collected to be tested for bacteriology of classical pathogenic bacteria; among the 50 animals, 34 produced a milk containing pathogenic bacteria, no pathogenic bacteria has been detected in the milk of the 16 remaining animals, it can nevertheless not be excluded that those 16 animals were infected by a non-tested pathogenic bacteria.

Results: No adverse effect of the treatment has been observed, it has been well tolerated. 16/50 animals have been cured (32%) after 3 or 4 administrations of HCA; among those animals, 7/34 animals which were bacteriologically positive at DO (assessed in milk sample collected for bacteriology before the treatment starts) were cured (20.6%) and 9/16 animals which were bacteriologically negative at DO were cured (56.3%).

Conclusion: This clinical field study highlights that HCA is able to treat infectious mastitis; it could thus be used as a first-line treatment to limit as much as possible the use of antibiotics and the onset of antimicrobial resistance.

EXAMPLE 3—SOLID LIPID NANOPARTICLES FORMULA

| Name of substances | Quantity percentage (% w/w) |
|---|---|
| Hydrocortisone aceponate | 0.058 |
| Precirol ATO 5 | 10.0 |
| Polysorbate 80 | 2.5 |
| Purified water buffered at pH 4.75 (acetate buffer) | QSP 100% |

EXAMPLE 4—IN SITU GELLING SYSTEM

| Name of substances | Quantity percentage (% w/w) |
|---|---|
| Hydrocortisone aceponate | 0.058 |
| Xanthan gum | 0.75 |
| Kolliphor P407 | 17.0 |
| Purified water buffered at pH 4.75 (acetate buffer) | QSP 100% |

EXAMPLE 5—MICELLAR SOLUTION

| Name of substances | Quantity percentage (% w/w) |
|---|---|
| Hydrocortisone aceponate | 0.1 |
| Polysorbate 80 | 5.0 |
| Purified water buffered at pH 4.75 (acetate buffer) | QSP 100% |

EXAMPLE 6—CYCLODEXTRIN INCLUSION COMPLEX FORMULATION

| Name of substances | Quantity percentage (% w/w) |
|---|---|
| Hydrocortisone aceponate | 0.1 |
| Hydroxypropyl-beta-cyclodextrin | 10.0 |
| Purified water buffered at pH 4 (acetate buffer) | QSP 100% |

EXAMPLES 7—EMULSIONS

Emulsion 1

| Name of substances | Quantity percentage (% w/w) |
|---|---|
| Hydrocortisone aceponate | 0.13 |
| Emulcire 61 WL 2659 | 4.0 |
| Apifil | 7.0 |
| Miglyol 812 N | 29.87 |
| Purified water buffered at pH 4.75 (acetate buffer) | QSP 100% |

Emulsion 2

| Name of substances | Quantity percentage (% w/w) |
|---|---|
| Hydrocortisone aceponate | 0.13 |
| Emulcire 61 WL 2659 | 3.0 |
| Gelot 64 | 3.0 |
| Cetyl alcohol | 3.0 |
| Miglyol 812 N | 14.87 |
| Purified water buffered at pH 4.75 (acetate buffer) | QSP 100% |

Emulsion 3

| Name of substances | Quantity percentage (% w/w) |
|---|---|
| Hydrocortisone aceponate | 0.13 |
| Emulcire 61 WL 2659 | 3.0 |
| Apifil | 5.0 |
| Miglyol 812 N | 29.87 |
| Purified water buffered at pH 4.75 (acetate buffer) | QSP 100% |

EXAMPLE 8: INTRAMAMMARY FORMULATIONS

| % w/w | A | B | C | D | E | F |
|---|---|---|---|---|---|---|
| Hydrocortisone aceponate | 0.22 | 0.23 | 0.21 | 0.21 | 0.4 | 0.46 |
| Vaseline oil | 68.6 | 40 | / | / | 40 | 40 |
| Miglyol 812N | / | / | QS100 | QS100 | / | / |
| Vaseline Codex T5 | / | / | / | / | QS100 | QS100 |
| Vaseline 7702 | 28.18 | QS100 | / | / | / | / |
| Aluminium monostearate | 3 | / | 10 | 5 | / | / |
| Thixin R | / | / | / | / | / | / |

| % w/w | G | H | I | J | K | L |
|---|---|---|---|---|---|---|
| Hydrocortisone aceponate | / | 0.23 | 0.23 | 0.23 | 0.23 | 0.23 |
| Vaseline oil | QS | 35 | 40 | 45 | 50 | 55 |
| Miglyol 812N | / | / | / | / | / | / |
| Vaseline Codex T5 | / | QS100 | QS100 | QS100 | QS100 | QS100 |
| Vaseline 7702 | / | / | / | / | / | / |
| Aluminium monostearate | / | / | / | / | / | / |
| Thixin R | 4 | / | / | / | / | / |

EXAMPLE 9: INTRAMAMMARY FORMULATIONS ASSOCIATED WITH ANTIBIOTICS

| % w/w | M | N | O | P | Q | R | S | T |
|---|---|---|---|---|---|---|---|---|
| Hydrocortisone aceponate | 0.23 | 0.23 | 0.23 | 0.23 | 0.23 | 0.23 | 0.23 | 0.23 |
| Cephalexin H2O microsterile | 2.49 | 2.49 | 2.49 | 2.49 | 2.49 | 2.49 | 2.49 | 2.49 |
| Sterile Kanamycine monosulfate | 1.88 | 1.88 | 1.88 | 1.88 | 1.88 | 1.88 | 1.88 | 1.88 |
| Vaseline oil | 60 | 60 | 60 | 70 | QS100 | / | / | QS100 |
| Liquid paraffin | / | / | / | / | / | QS100 | / | / |
| Miglyol 812N | / | / | / | / | / | / | QS100 | / |
| Vaseline Codex T5 | QS100 | QS100 | / | / | / | / | / | / |
| Vaseline 7702 | / | / | QS100 | QS100 | / | / | / | / |
| Aluminium monostearate | / | 3 | / | 3 | 7.5 | 7.5 | 7.5 | / |
| Thixin R | / | / | / | / | / | / | / | 3.5 |

EXAMPLE 10: IN SITU GELLING PHOSPHOLIPID SYSTEMS FOR OTIC ADMINISTRATION

| Name of substances | | A (% w/w) | B (% w/w) | C (% w/w) | D (% w/w) | E (% w/w) |
|---|---|---|---|---|---|---|
| Hydrocortisone aceponate | Active | 0.0584 | 0.0584 | 0.0584 | 0.0584 | 0.0584 |
| Phospholipon 90G | Jellifying agent | 70 | 50 | 70 | 36  60 | 25 |
| Isopropyl myristate | Solvent | — | QSP100 | 15 | 54 | QSP100 |
| Ethanol | Solvent | QSP100 | — | QSP100 | QSP100 | — |

EXAMPLE 11: JELLIFIED FORMULATIONS FOR OTIC ADMINISTRATION

System 1

| Name of substances | Quantity percentage (% w/V) |
|---|---|
| Hydrocortisone aceponate | 0.0584 |
| PVPK90 | 2 |
| Dowanol | QS 100 |

Said formulation provided an improved viscosity by 7 compared to Cortavance®

System 2

| Name of substances | Quantity percentage (% w/V) |
|---|---|
| Hydrocortisone aceponate | 0.0584 |
| PVPK90 | 1 |
| Glycerol | 10 |
| Dowanol | QS 100 |

Said formulation provided an improved viscosity by 12 compared to the Cortavance® formulation.

Such formulations with an increased viscosity enable to increase the residence time of the product in the ear, hence increase the duration of activity of the product. This presents the advantage of enabling reduced number of administration.

Said systems 1 and 2 were tested for in vivo tolerance in dogs. The formulations were administered at a dose of 1 ml once a day during 3 consecutive days in dog ear and were well tolerated.

The invention claimed is:

1. A method for the treatment and/or the prevention of an epithelial microbial infection of the ear in a non-human mammal in need thereof, the method comprising topically administering in the ear to be treated an effective amount of hydrocortisone or a salt thereof to the non-human mammal, wherein said epithelial microbial infection is otitis externa, wherein the effective amount of hydrocortisone or its salt is between 0.1 and 0.5 mg and is administered at least once a week when said method is for prevention, and/or is administered once a day up to 20 consecutive days when said method is for treatment.

2. A method for the treatment and/or the prevention of an epithelial microbial infection of the ear in a non-human mammal in need thereof, the method comprising topically administering in the ear to be treated an effective amount of hydrocortisone or a salt thereof to the non-human mammal, wherein said epithelial microbial infection is otitis externa, wherein said hydrocortisone or a salt thereof is formulated in a pharmaceutical composition also comprising a pharmaceutically acceptable carrier and wherein said composition does not contain any antibiotic agent, antifungal agent, antiviral agent or antimicrobial agent.

3. The method as in claim 1 or 2, wherein said epithelial microbial infection of the ear is caused by bacteria, fungi and/or yeasts.

4. The method as in claim 1 or 2, wherein said epithelial microbial infection of the ear is caused by bacteria.

5. The method of claim 4, wherein the bacteria is selected in the group comprising Gram-positive bacteria, and/or Gram-negative bacteria.

6. The method as in claim 1 or 2, wherein said epithelial microbial infection of the ear is caused by fungi and/or yeasts.

7. The method as in claim 1 or 2, wherein said non-human mammal is a dog or a cat.

8. The method of claim 2 for the treatment of otitis externa, wherein the effective amount of hydrocortisone or its salt is between 0.01 and 10 mg and is administered once or twice a day up to 20 consecutive days.

9. The method of claim 2 for the prevention of otitis externa, wherein the effective amount of hydrocortisone or its salt is between 0.01 and 10 mg and is administered at least once a week.

10. The method of claim 2, comprising administering by topical application the pharmaceutical composition onto an epithelial area inside the ear.

11. The method of claim 2, wherein the microbial infection of the ear is caused by bacteria.

12. The method of claim 5, wherein the Gram-positive bacteria is *Staphylococcus aureus* or *Streptococcus* spp.

13. The method of claim 5, wherein the Gram-negative bacteria is *Escherichia coli*.

14. The method of claim 11, wherein the bacteria is a Gram-positive bacteria.

15. The method of claim 14, wherein the Gram positive bacteria is selected from *Staphylococcus aureus* and *Streptococcus* spp.

16. The method of claim 11, wherein the bacteria is a Gram-negative bacteria.

17. The method of claim 16, wherein the Gram-negative bacteria is *Escherichia coli*.

* * * * *

UNITED STATES PATENT AND TRADEMARK OFFICE
CERTIFICATE OF CORRECTION

| | | |
|---|---|---|
| PATENT NO. | : 11,819,506 B2 | Page 1 of 1 |
| APPLICATION NO. | : 17/263516 | |
| DATED | : November 21, 2023 | |
| INVENTOR(S) | : Havrileck et al. | |

It is certified that error appears in the above-identified patent and that said Letters Patent is hereby corrected as shown below:

On the Title Page

| Column | Line | |
|---|---|---|
| Item (57), Abstract | 3 | change "organ having" to -- organs having -- |

Signed and Sealed this
Eleventh Day of November, 2025

John A. Squires
*Director of the United States Patent and Trademark Office*